(12) United States Patent
Yamada

(10) Patent No.: US 9,702,982 B2
(45) Date of Patent: Jul. 11, 2017

(54) CONTROL APPARATUS, RADIATION IMAGING APPARATUS, RADIATION IMAGING SYSTEM AND CONTROL METHOD

(71) Applicant: CANON KABUSHIKI KAISHA, Tokyo (JP)

(72) Inventor: Naoki Yamada, Soka (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 102 days.

(21) Appl. No.: 14/661,091

(22) Filed: Mar. 18, 2015

(65) Prior Publication Data

US 2015/0276938 A1  Oct. 1, 2015

(30) Foreign Application Priority Data

Mar. 31, 2014 (JP) ................................ 2014-073730

(51) Int. Cl.
 *G01T 1/17* (2006.01)
 *A61B 6/00* (2006.01)
 *G06F 19/00* (2011.01)
(52) U.S. Cl.
 CPC ................ *G01T 1/17* (2013.01); *A61B 6/563* (2013.01); *G06F 19/321* (2013.01); *G06F 19/3406* (2013.01)

(58) Field of Classification Search
 CPC .... G06F 19/321; G06F 19/3406; A61B 6/563
 See application file for complete search history.

(56) References Cited

U.S. PATENT DOCUMENTS

| 8,229,063 | B2 * | 7/2012 | Nishii | ................... | H04L 1/1848 |
| | | | | | 378/19 |
| 2010/0088593 | A1 | 4/2010 | Nishii | ........................... | 715/273 |
| 2013/0230141 | A1 | 9/2013 | Miyachi | ........................ | 378/62 |

FOREIGN PATENT DOCUMENTS

| JP | 2010-088027 | 4/2010 |
| JP | 2013-180134 | 9/2013 |

* cited by examiner

*Primary Examiner* — Tony Ko
(74) *Attorney, Agent, or Firm* — Fitzpatrick, Cella, Harper & Scinto

(57) ABSTRACT

A control apparatus which receives a radiation image from a radiation imaging apparatus determines, at the time of activation, whether any unreceived radiation image to be received from the radiation imaging apparatus exists. Upon determining that an unreceived radiation image exists, the control apparatus requests the radiation imaging apparatus to transmit the radiation image.

22 Claims, 15 Drawing Sheets

CONTROL APPARATUS, RADIATION IMAGING APPARATUS, RADIATION IMAGING SYSTEM AND CONTROL METHOD

BACKGROUND OF THE INVENTION

Field of the Invention

The present invention relates to a radiation imaging system which obtains a radiation image of an object by irradiating it with radiation, a control apparatus, a radiation imaging apparatus and a control method.

Description of the Related Art

Recently, a radiation imaging system has been used in various fields, and has become an important means for diagnosis especially in the medical field. A radiation imaging system in the medical field is configured to irradiate, from an irradiating unit, an object with the radiation generated by a radiation generating apparatus and obtain a radiation image by sensing the radiation transmitted through the object using a radiation imaging apparatus. The control apparatus of the radiation imaging system performs image processing for the radiation image obtained in this manner and displays the resultant image on, for example, a monitor, thereby making the radiation image useful for diagnosis.

The above radiation imaging system sometimes uses a packet communication network for the transfer of a radiation image from the radiation imaging apparatus to the control apparatus in order to promote downsizing and generalization of transmission lines, wireless communication, and the like. The above packet communication is the communication operation of dividing data into small units and transmitting/receiving the data units one by one. Each divided data described above is called a packet.

In order to reliably transmit data to the control apparatus by using a packet communication network, a protocol having a retransmission function such as TCP (Transmission Control Protocol) is generally used. However, when using TCP, it is difficult to increase a date rate for retransmission handling. TCP is one of the Internet standard protocols which form a reliable connection between processes of transmission and reception hosts and perform retransmission or the like at the occurrence of a data loss. This protocol is high in reliability but low in transmission efficiency. In addition, the protocol suffers large packet arrival delays and sometimes cannot meet the requirement to display in real time.

For this reason, UDP (User Datagram Protocol) is used to achieve a reduction in delay. However, UDP generates no connection and makes no acknowledgement. For this reason, this protocol has a risk of a packet loss even though it can perform high-speed transmission. UDP is a connectionless communication designed only for the transmission/reception of data between applications, and is one of the Internet standard protocols which entrust reliability to applications. This protocol is low in reliability but high in transmission efficiency.

As described above, when a packet is lost at the time of transmission/reception of data by using UDP communication, the data transferred from the transmission side sometimes does not normally arrive at the reception side. That is, when a packet loss occurs in a radiation imaging system, the radiation image transmitted from the radiation imaging apparatus does not normally arrive at the control apparatus. A study has been made on a technique of retransmitting packet data on the UDP layer as a method of solving this problem. This method is disclosed in Japanese Patent Laid-Open Nos. 2010-088027 and 2013-180134.

However, the packet loss is not the only cause of the situation in which the radiation image transmitted from the radiation imaging apparatus does not normally arrive at the control apparatus. For example, when an abnormality occurs on the control apparatus side or unintentional power discontinuity occurs during the transmission of a radiation image from the radiation imaging apparatus to the control apparatus, the control apparatus side may not receive the radiation image transmitted from the radiation imaging apparatus. When such a situation occurs, even if an object is irradiated with radiation, the radiation image does not arrive at the control apparatus. As a consequence, the radiation image is lost, and the object undergoes ineffective exposure. In addition, when the radiation image is lost, it is necessary to image the object again. That is, the operator needs to perform imaging all over again, resulting in an operation time loss.

SUMMARY OF THE INVENTION

An embodiment of the present invention provides a radiation imaging system which can normally retransmit a radiation image even at the occurrence of an abnormality at the time of the transmission of the radiation image, a control apparatus, and a control method.

According to one aspect of the present invention, there is provided a control apparatus which receives a radiation image from a radiation imaging apparatus, the control apparatus comprising: a storage unit configured to store examination information and a radiation image received from the radiation imaging apparatus in accordance with the examination information; a determination unit configured to determine whether any unreceived radiation image exists, at the time of activation, based on a storage state of a radiation image corresponding to the examination information in the storage unit; and a request unit configured to request the radiation imaging apparatus to transmit a radiation image when the determination unit determines that the unreceived radiation image exists.

According to another aspect of the present invention, there is provided a radiation imaging apparatus comprising: a storage unit configured to store a radiation image obtained by radiation imaging; a determination unit configured to determine whether an untransmitted radiation image exists in the storage unit, when starting to establish a communication connection to a control apparatus; and a transmitting unit configured to transmit the untransmitted radiation image to the control apparatus in accordance with the start of the communication connection, if the determination unit determines that an untransmitted radiation image exists.

According to another aspect of the present invention, there is provided a radiation imaging apparatus which transmits an obtained radiation image to a control apparatus, the apparatus comprising: a receiving unit configured to receive identification information of an apparatus at a transfer destination from the control apparatus; a storage unit configured to store a radiation image obtained by radiation imaging; and a transmitting unit configured to transmit the stored radiation image to the apparatus at the transfer destination based on the identification information, when transmission of the radiation image stored in the storage unit to the control apparatus fails.

According to another aspect of the present invention, there is provided a radiation imaging apparatus which transmits an obtained radiation image to a control apparatus, the apparatus comprising: a receiving unit configured to receive identification information of an imaging order from the control apparatus; a storage unit configured to store a radiation image obtained by radiation imaging and the identification information in association with each other; and a transmitting unit configured to transmit the stored radiation image and the identification information to an external apparatus in accordance with a transmission request of the radiation image from the external apparatus, when transmission of the radiation image stored in the storage unit to the control apparatus fails.

According to another aspect of the present invention, there is provided a control method for a control apparatus which receives a radiation image from a radiation imaging apparatus, the method comprising: a determination step of determining whether an unreceived radiation image to be received from the radiation imaging apparatus exists, at the time of activation; and a request step of requesting the radiation imaging apparatus to transmit a radiation image, if it is determined in the determination step that the unreceived radiation image exists.

According to another aspect of the present invention, there is provided a control method for a radiation imaging apparatus, the method comprising: a storing step of storing a radiation image obtained by radiation imaging in a storage unit; a determination step of determining whether an untransmitted radiation image exists in the storage unit, when starting to establish a communication connection to a control apparatus; and a transmitting step of transmitting the untransmitted radiation image to the control apparatus in accordance with the start of the communication connection, if it is determined in the determination step that an untransmitted radiation image exists.

According to another aspect of the present invention, there is provided a control method for a radiation imaging apparatus which transmits an obtained radiation image to a control apparatus, the method comprising: a receiving step of receiving identification information of an apparatus at a transfer destination from the control apparatus; a storing step of storing a radiation image obtained by radiation imaging in a storage unit; and a transmitting step of transmitting the stored radiation image to the apparatus at the transfer destination based on the identification information, when transmission of the radiation image stored in the storage unit to the control apparatus fails.

According to another aspect of the present invention, there is provided a control method for a radiation imaging apparatus which transmits an obtained radiation image to a control apparatus, the method comprising: a receiving step of receiving identification information of an imaging order from the control apparatus; a storing step of storing a radiation image obtained by radiation imaging and the identification information in a storage unit in association with each other; and a transmitting step of transmitting the stored radiation image and the identification information to an external apparatus in accordance with a transmission request of the radiation image from the external apparatus, when transmission of the radiation image stored in the storage unit to the control apparatus fails.

According to another aspect of the present invention, there is provided a radiation imaging system in which a control apparatus receives a radiation image from a radiation imaging apparatus via a network, the control apparatus comprising: a determination unit configured to determine, at the time of activation, whether an unreceived radiation image to be received from the radiation imaging apparatus exists; and a request unit configured to request the radiation imaging apparatus to transmit a radiation image when the determination unit determines that the unreceived radiation image exists.

According to another aspect of the present invention, there is provided a radiation imaging system in which a control apparatus receives a radiation image from a radiation imaging apparatus via a network, the radiation imaging apparatus comprising: a storage unit configured to store a radiation image obtained by radiation imaging; a determination unit configured to determine whether an untransmitted radiation image exists in the storage unit, when starting to establish a communication connection to a control apparatus; and a transmitting unit configured to transmit the untransmitted radiation image to the control apparatus in accordance with the start of the communication connection, if the determination unit determines that an untransmitted radiation image exists.

According to another aspect of the present invention, there is provided a radiation imaging system in which a control apparatus receives a radiation image from a radiation imaging apparatus via a network, the radiation imaging apparatus comprising: a receiving unit configured to receive identification information of an apparatus at a transfer destination from the control apparatus; a storage unit configured to store a radiation image obtained by radiation imaging; and a transmitting unit configured to transmit the stored radiation image to the apparatus at the transfer destination based on the identification information, when transmission of the radiation image stored in the storage unit to the control apparatus fails.

According to another aspect of the present invention, there is provided a radiation imaging system in which a control apparatus receives a radiation image from a radiation imaging apparatus via a network, the radiation imaging apparatus comprising: a receiving unit configured to receive identification information of an imaging order from the control apparatus; a storage unit configured to store a radiation image obtained by radiation imaging and the identification information in association with each other; and a transmitting unit configured to transmit the stored radiation image and the identification information to an external apparatus in accordance with a transmission request of the radiation image from the external apparatus, when transmission of the radiation image stored in the storage unit to the control apparatus fails.

Further features of the present invention will become apparent from the following description of exemplary embodiments (with reference to the attached drawings).

DESCRIPTION OF THE EMBODIMENTS

Several preferred embodiments of the present invention will be described below with reference to the accompanying drawings.

First Embodiment

Figure 1:
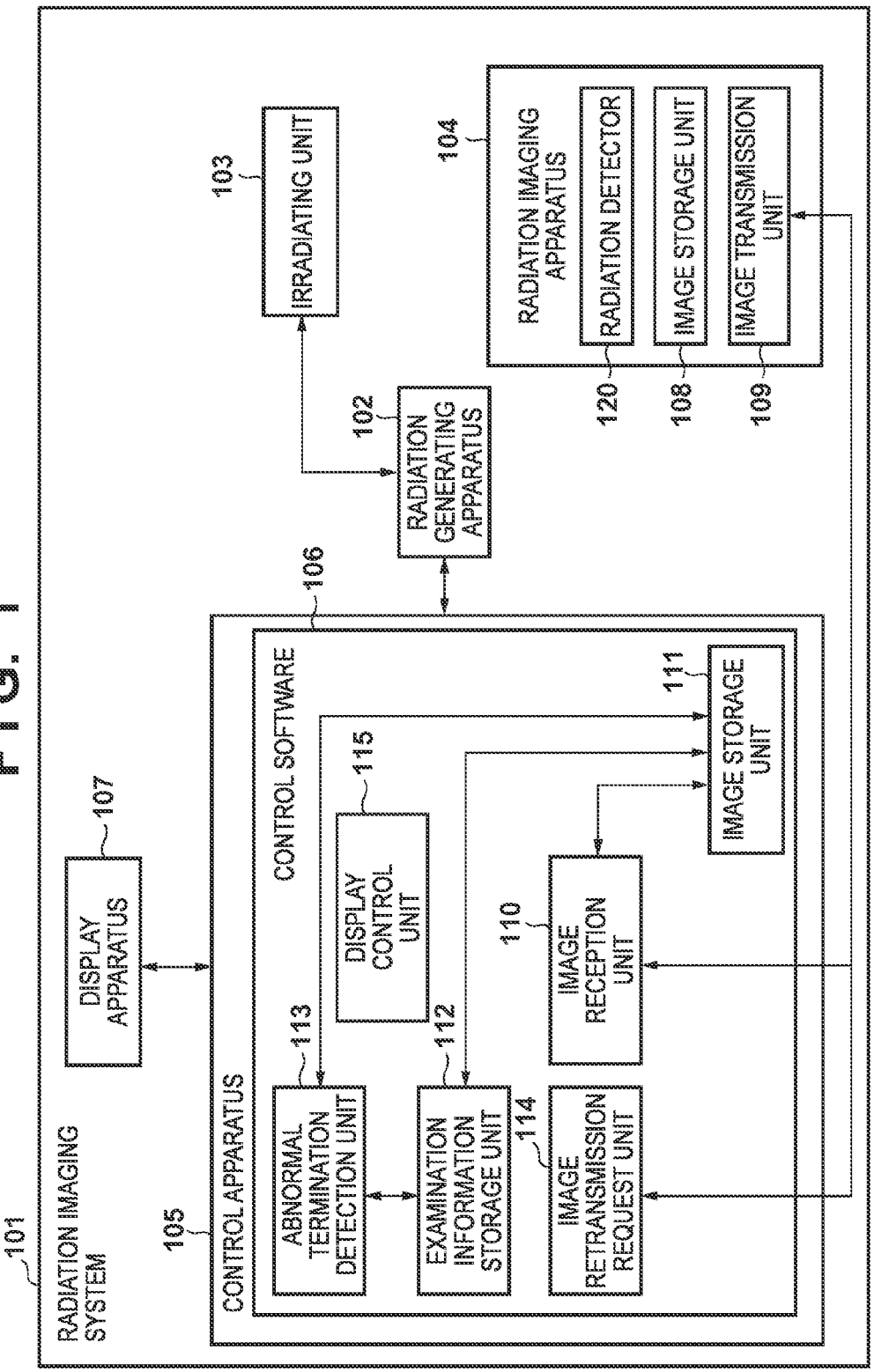
FIG. 1 is a block diagram showing an example of the arrangement of a radiation imaging system according to the first embodiment.

FIG. 1 is a block diagram showing an example of the arrangement of a radiation imaging system according to the first embodiment. A radiation imaging system 101 includes a radiation generating apparatus 102, an irradiating unit 103, a radiation imaging apparatus 104, a control apparatus 105, and a display apparatus 107.

The radiation generating apparatus 102 has a radiation source, and generates radiation in accordance with an exposure signal from the control apparatus 105. The irradiating unit 103 irradiates an object with the radiation generated by the radiation generating apparatus 102. The radiation imaging apparatus 104 includes a radiation detector 120 which converts the dose of radiation arriving at the detection surface into an electrical signal, and obtains a radiation image. An image storage unit 108 temporarily stores an obtained radiation image. An image transmission unit 109 transmits the radiation image stored in the image storage unit 108 to the control apparatus 105. The display apparatus 107 executes various types of display such as the display of an obtained radiation image under the control of the control apparatus. The display apparatus 107 also functions as a GUI (Graphical User Interface).

Figure 2:
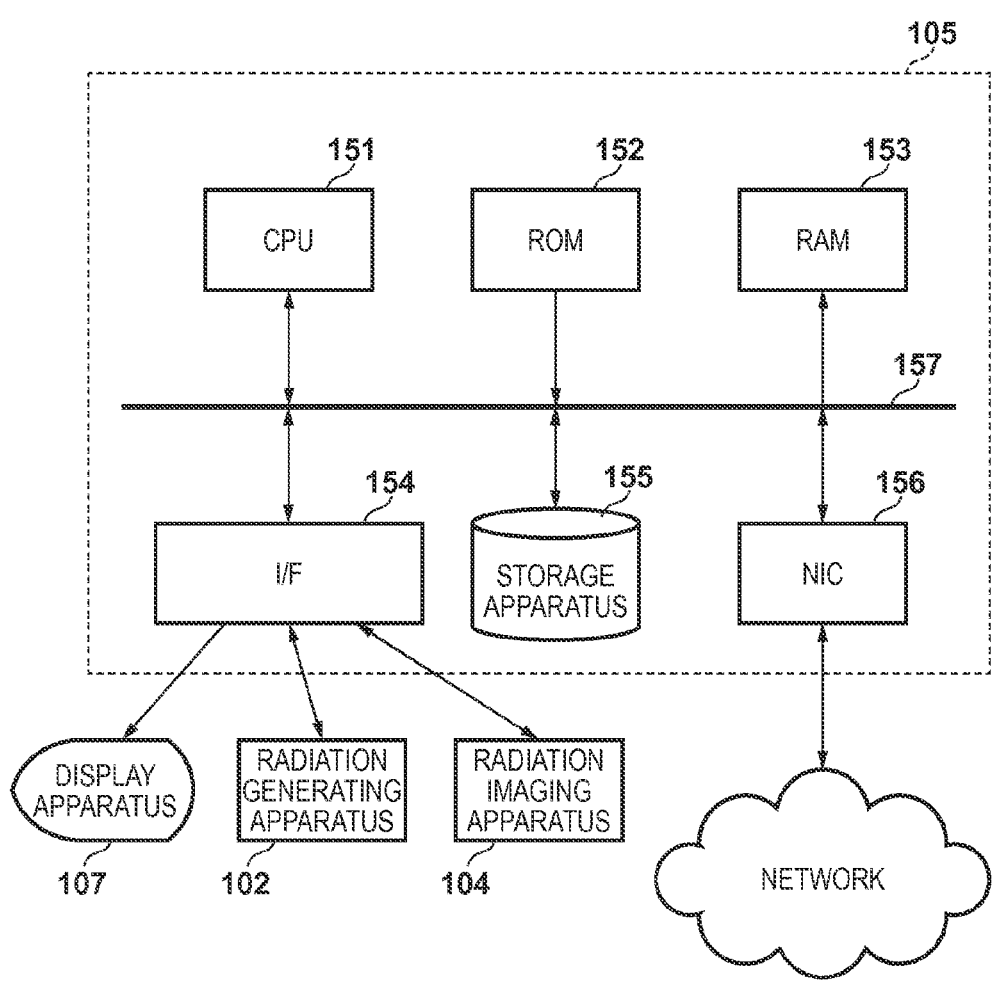
FIG. 2 is a block diagram showing an example of the hardware configuration of a control apparatus.

The control apparatus 105 controls the execution of radiation imaging by controlling the radiation generating apparatus 102 and the radiation imaging apparatus 104. FIG. 2 shows an example of the hardware configuration of the control apparatus 105. Referring to FIG. 2, a CPU 151 implements various types of control (the respective functional units of control software 106 shown in FIG. 1) by executing programs stored in a ROM 152 and a RAM 153. The ROM 152 is a read-only nonvolatile memory. The RAM 153 is a readable/writable volatile memory.

An interface 154 connects the radiation generating apparatus 102, the radiation imaging apparatus 104, and the display apparatus 107 to the control apparatus 105. A storage apparatus 155 includes, for example, a hard disk and stores various types of data. For example, an image storage unit 111 can be implemented by the storage apparatus 155. A network interface (NIC 156) connects the control apparatus to a network such as the Internet. The above units are communicably connected to each other via a bus 157.

Referring back to FIG. 1, the control apparatus 105 implements the respective functional units such as an image reception unit 110, the image storage unit 111, an examination information storage unit 112, an abnormal termination detection unit 113, and an image retransmission request unit 114 by causing the CPU 151 to execute the control software 106. Note that some or all of these functional units may be implemented by dedicated hardware and the like.

The image reception unit 110 receives the radiation image transmitted from the image transmission unit 109 of the radiation imaging apparatus 104. The image storage unit 111 stores the radiation image received by the image reception unit 110 in, for example, the storage apparatus 155. The examination information storage unit 112 stores, in, for example, the storage apparatus 155, examination information including the object information of the object imaged by the radiation imaging system 101 and an imaging part. The abnormal termination detection unit 113 detects whether the control software 106 is abnormally terminated. In this case, abnormal termination includes, for example, a case in which the control software 106 is abnormally terminated when power supplied to the control apparatus 105 is interrupted at an unintended timing and a case in which an abnormality has occurred in the control software 106 itself. The image retransmission request unit 114 is arranged in the control apparatus 105, and requests the image transmission unit 109 to retransmit a radiation image. A display control unit 115 controls the execution of various types of display by the display apparatus 107.

A general radiation imaging procedure in the radiation imaging system 101 will be described next. Note that the radiation imaging procedure described below is a normal imaging procedure without any abnormal termination detected by the abnormal termination detection unit 113. First of all, the operator inputs examination information such as the object information of an object, an imaging part, and the identification information of the radiation imaging apparatus 104 to be used via the display screen (GUI) displayed on the display apparatus 107, and issues an instruction to start an examination. The display screen is displayed on the display apparatus 107 via the display control unit 115 by the control apparatus 105 which executes the control software 106. Note that the input examination information is stored in the examination information storage unit 112.

After the start of the examination, the operator properly positions the object such that the radiation irradiated from the irradiating unit 103 is transmitted through the object, and the radiation transmitted through the object enters the radiation imaging apparatus 104. The operator then presses a radiation irradiation switch (not shown) to obtain a radiation image of the object. That is, the radiation transmitted through the object is visualized by the radiation imaging apparatus 104 to obtain a radiation image of the object. The obtained radiation image is stored in the image storage unit 108 in the radiation imaging apparatus 104, and is transmitted to the control apparatus 105 by the image transmission unit 109.

The control software 106 operates on the control apparatus 105. The image reception unit 110 receives the radiation image transmitted from the image transmission unit 109. The image storage unit 111 stores the image. The radiation image stored in the image storage unit 111 and the examination information stored in the examination information storage unit 112 are managed as relevant data. In addition, it is possible to display, on the display apparatus 107, the radiation image stored in the image storage unit 111 and the examination information stored in the examination information storage unit 112. The operator can browse, via the display apparatus 107, the radiation image of the object which is obtained by radiation irradiation and the examination information associated with the radiation image. In this manner, the radiation imaging system executes radiation imaging. Note that in the radiation imaging system 101, a connection for the transmission/reception of an image from the image transmission unit 109 to the image reception unit 110 may be either a wired connection or a wireless connection.

Figure 3:
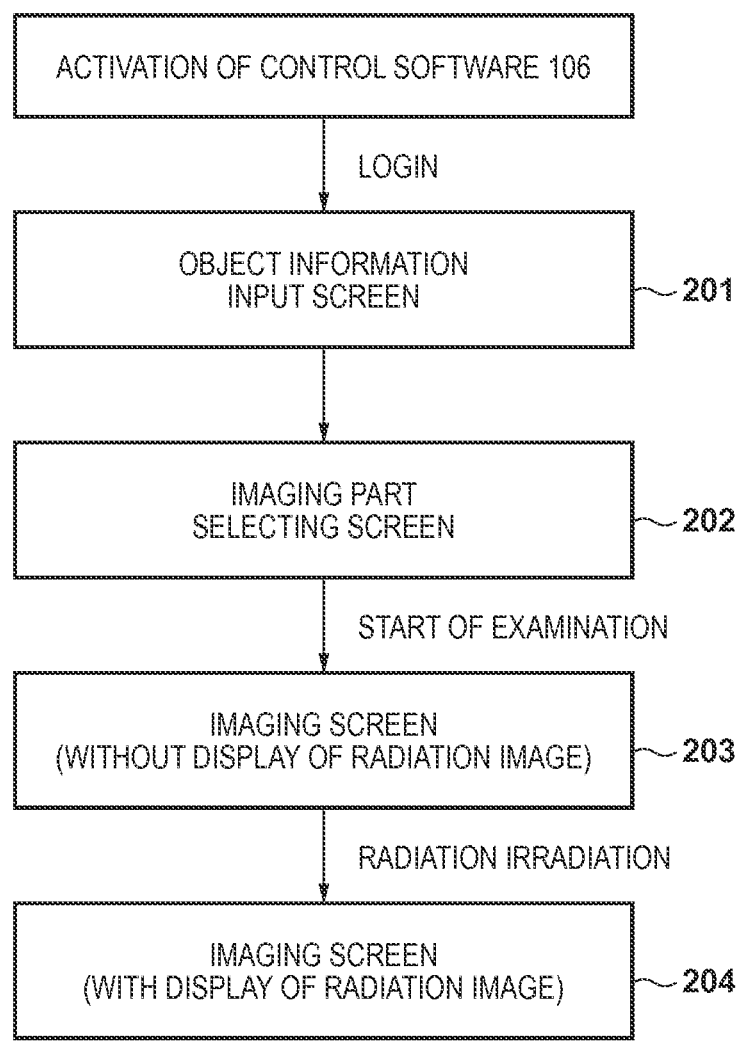
FIG. 3 is a view for explaining a display screen transition according to the first embodiment.

FIG. 3 shows an example of display screen transition by the control apparatus 105 which executes the control software 106. An object information input screen 201 (FIG. 4) is displayed when object information is input in the imaging procedure described above. An imaging part selecting screen 202 is displayed when an imaging part and a radiation imaging apparatus are selected in the imaging procedure described above. When the operator completely inputs examination information such as object information, an imaging part, and the identification information of a radiation imaging apparatus to be used by using the object information input screen 201 and the imaging part selecting screen 202 (FIG. 5), and issues an instruction to start an examination, the control apparatus 105 displays an imaging screen 203 (FIG. 6) on the display apparatus 107. The imaging screen 203 is a screen to be displayed at the start of an examination, which displays no radiation image because no radiation irradiation is executed. When radiation irradiation is executed in the state of the imaging screen 203, the screen shifts to the state of an imaging screen 204 (FIG. 7) displaying a radiation image.

Figure 4:
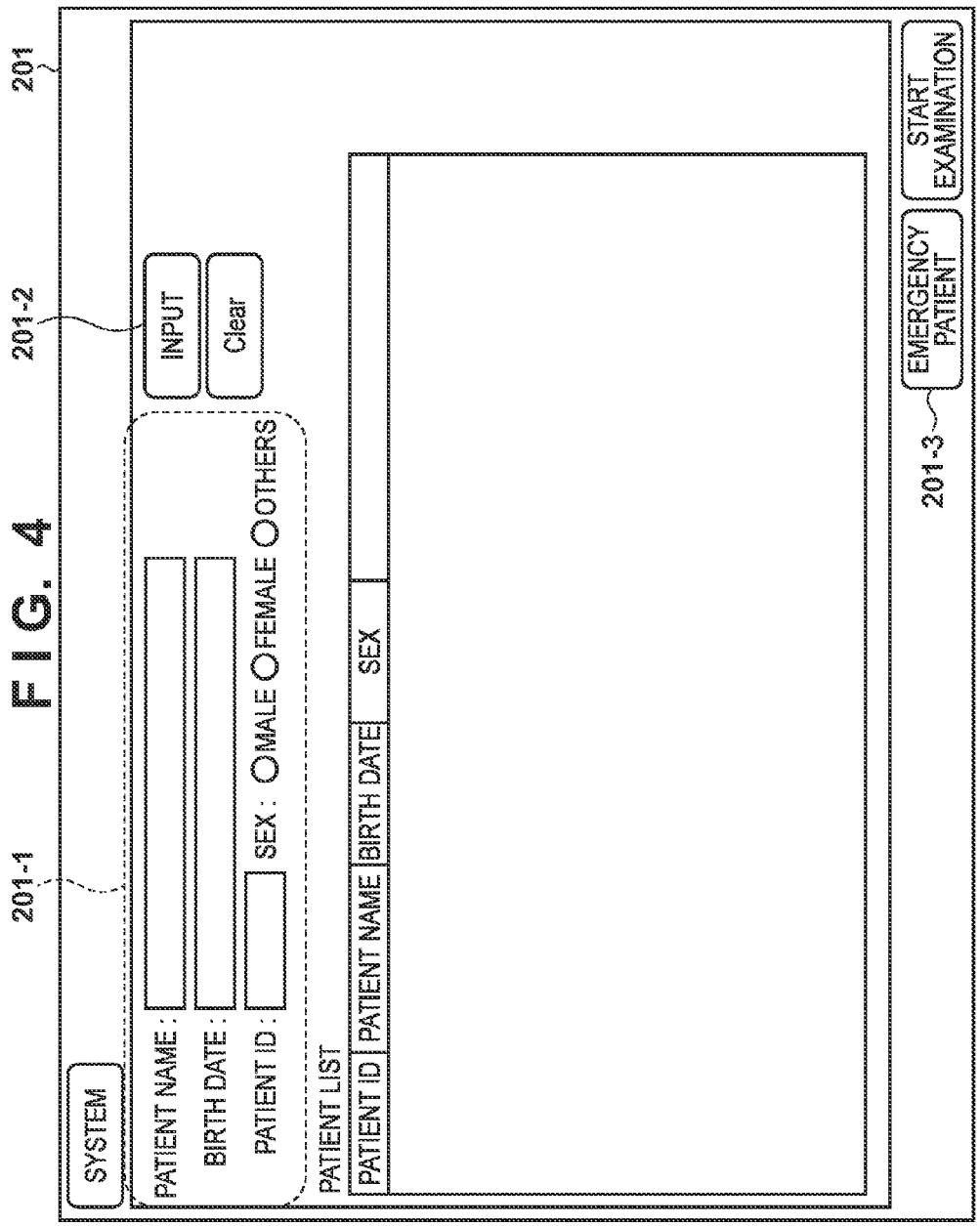
FIG. 4 is a view showing an object information input screen.

FIG. 4 shows an example of the object information input screen 201. When the operator inputs a patient name, a birth date, a patient ID, sex, and the like as object information into an input field 201-1 in FIG. 4 and presses an input button 201-2, the screen shifts to the imaging part selecting screen 202. When the operator presses an emergency patient button 201-3, the screen can shift to the imaging part selecting screen 202 with object information prepared for an emergency patient.

Figure 5:
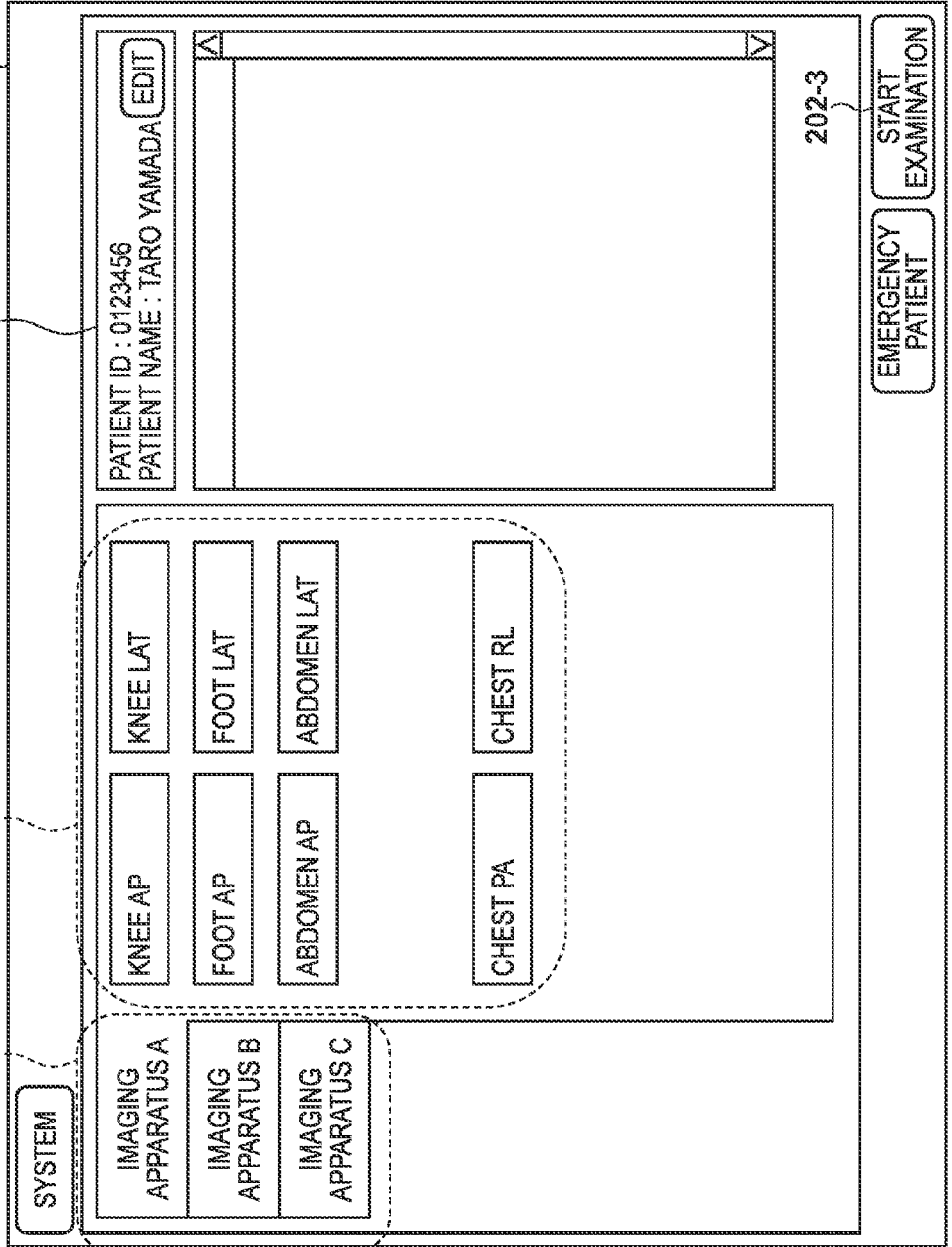
FIG. 5 is a view showing an imaging part selecting screen.

FIG. 5 shows an example of the imaging part selecting screen 202. When the operator presses an examination start button 202-3 upon selecting a radiation imaging apparatus to be used from an imaging apparatus group 202-1, and an imaging part from an imaging part group 202-2, the screen shifts to the imaging screen (without the display of a radiation image) 203. Note that a display area 202-4 displays the object information input on the object information input screen 201 (the object information prepared for an emergency patient when the screen has shifted upon pressing the emergency patient button 201-3).

Figure 6:
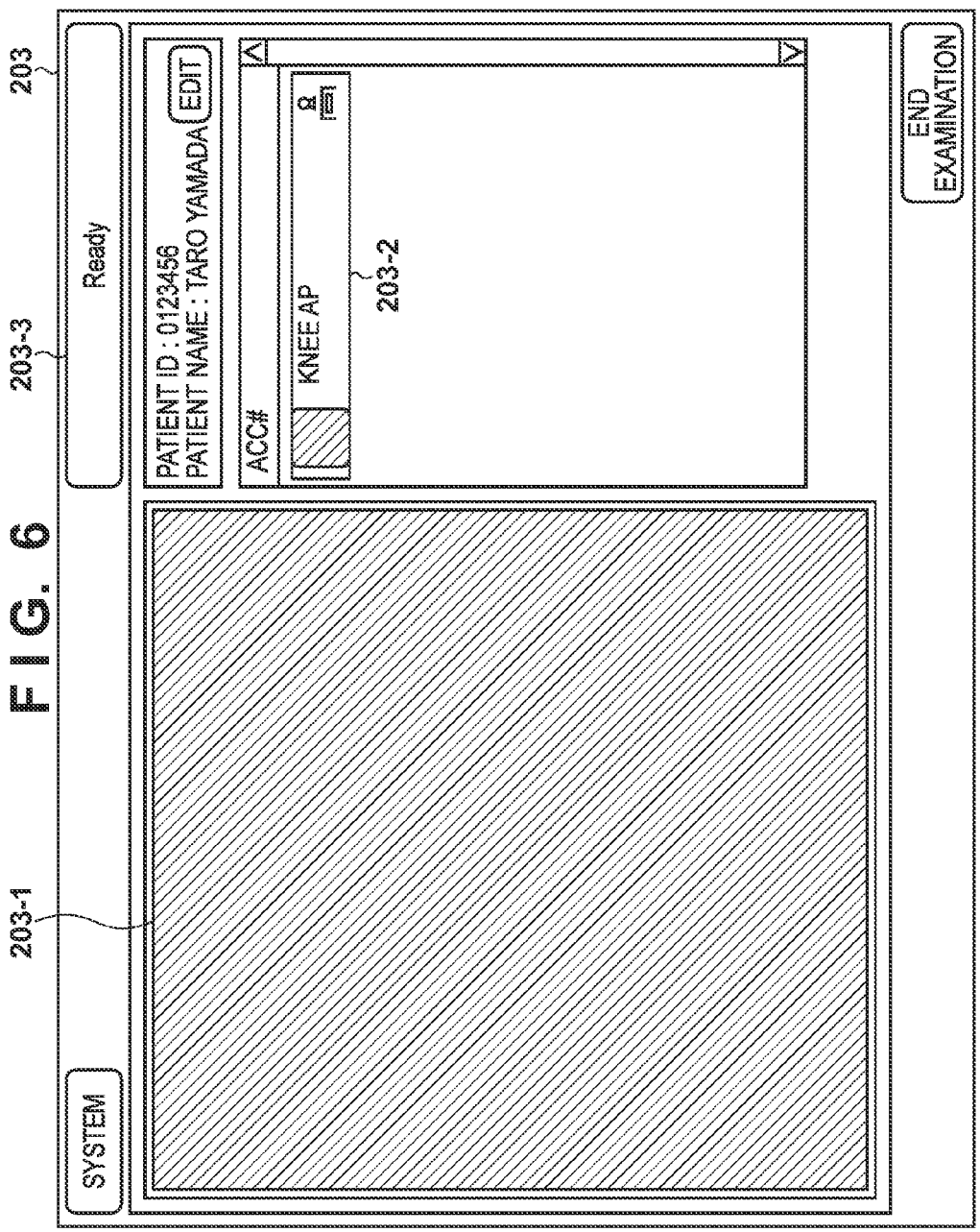
FIG. 6 is a view showing an imaging screen (without the display of a radiation image)

FIG. 6 shows an example of the imaging screen (without the display of a radiation image) 203. A display area 203-1 for a radiation image displays nothing because no radiation irradiation has been executed on the imaging screen (without the display of a radiation image) 203. In addition, a display area 203-2 displays examination information based on the imaging part selected on the imaging part selecting screen 202. A display area 203-3 displays the state of the radiation imaging apparatus selected on the imaging part selecting screen 202.

Figure 7:
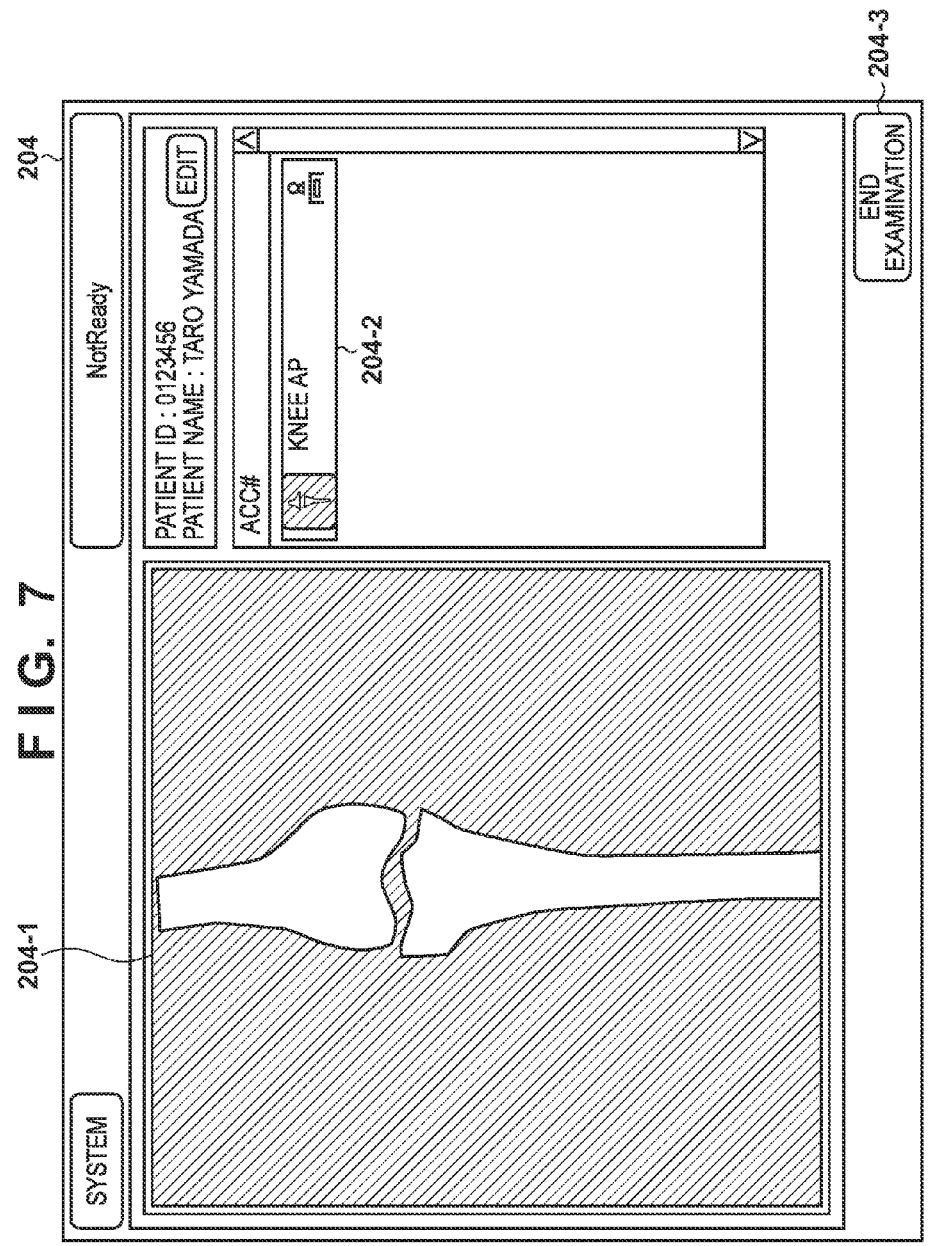
FIG. 7 is a view showing an imaging screen (with the display of a radiation image)

FIG. 7 shows an example of the imaging screen (with the display of a radiation image) 204. A display area 204-1 displays the radiation image obtained by the radiation imaging apparatus upon radiation irradiation. In addition, a display area 204-2 also displays a thumbnail of the obtained radiation image. Note that the operator can terminate a series of examination operations by pressing an examination termination button 204-3 and return to the object information input screen 201.

Figure 8:
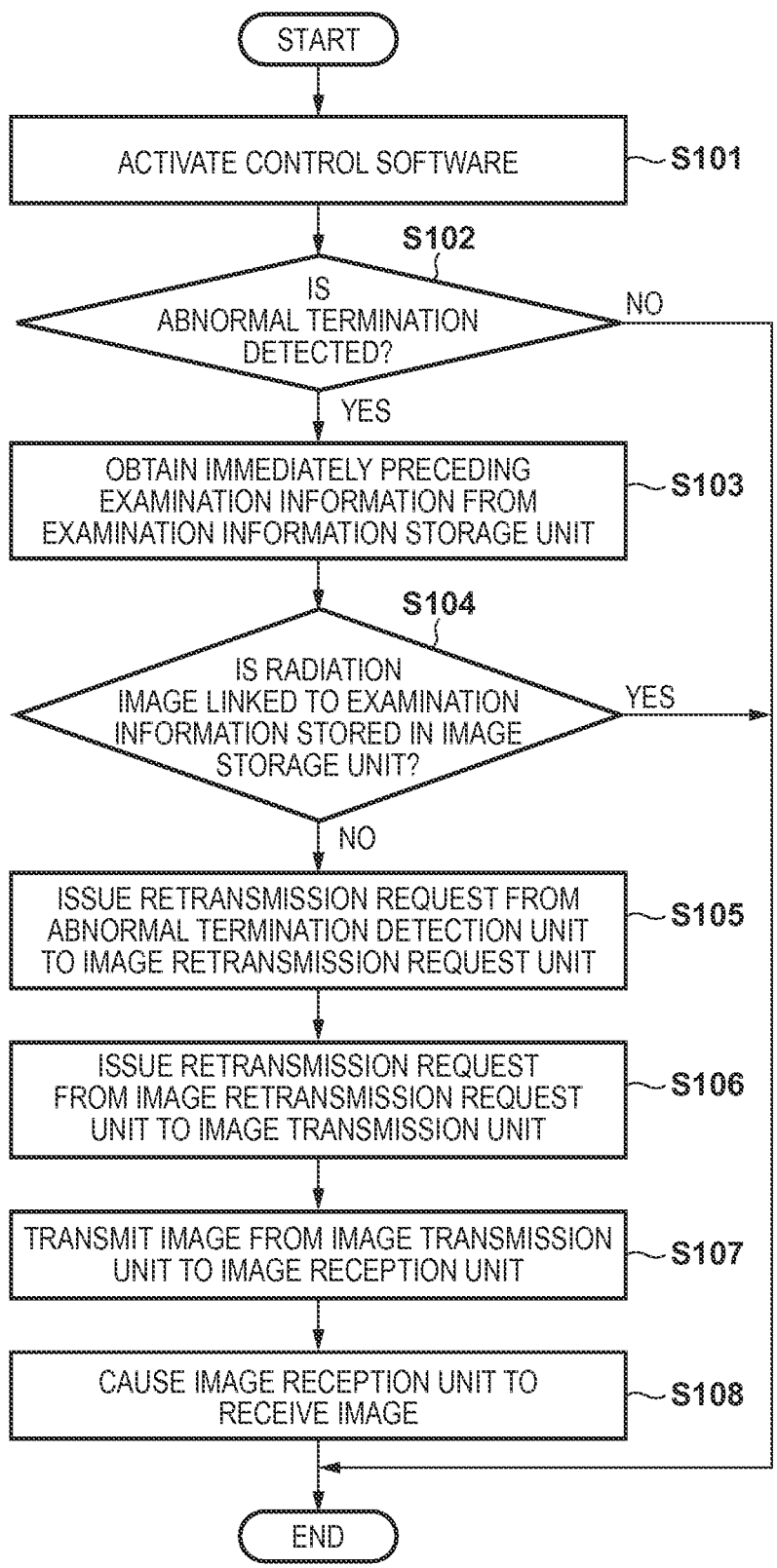
FIG. 8 is a flowchart for explaining the operation of the control apparatus according to the first embodiment.

Retransmission processing for a radiation image to be performed when the control software 106 is abnormally terminated during the transfer of a radiation image in the radiation imaging system in FIG. 1 will be described next with reference to the flowchart of FIG. 8.

When the control software 106 is activated (step S101), the abnormal termination detection unit 113 detects whether the control software 106 has abnormally been terminated during the transmission of a radiation image (step S102). For example, an abnormal termination detection method is performed as follows: setting a normal termination flag at a normal termination time, and determining that the previous termination is an abnormal termination, when the normal termination flag is not set at the time of activation. Note that the abnormal termination detection method to be used is not limited to the above method as long as it is possible to determine that the previous termination is an abnormal termination. In addition, determination of activation in step S101 may be performed either when the apparatus is powered on to activate the control software 106 or when the control software 106 is activated before or after the display of a predetermined screen or by a predetermined operation (the operation of a predetermined activation switch). Note that the predetermined screen is, for example, a "screen for inputting patient information" or a "screen for displaying a list of examination orders".

If the abnormal termination detection unit 113 determines, at the time of the activation of the control software 106, that the previous termination is an abnormal termination (steps S101 and S102), the abnormal termination detection unit 113 determines in steps S103 and S104 whether any unreceived radiation image exists, which should be received from the radiation imaging apparatus 104. According to this embodiment, the abnormal termination detection unit 113 determines whether any unreceived radiation image exists, based on the storage state of radiation images in the image storage unit 111, which stores the radiation images received from the radiation imaging apparatus 104. More specifically, the abnormal termination detection unit 113 operates as follows.

The abnormal termination detection unit 113 reads out examination information associated with the radiation image transmitted immediately before the abnormal termination of the control software 106 from the examination information storage unit 112 (step S103). The abnormal termination detection unit 113 then confirms whether the radiation image corresponding to the examination information obtained in step S103 is stored in the image storage unit 111 (step S104). If the radiation image corresponding to the examination information obtained in step S103 is not stored in the image storage unit 111, the abnormal termination detection unit 113 determines that an unreceived radiation image exists, which should be received from the radiation imaging apparatus 104. Upon determining that an unreceived radiation image exists, the abnormal termination detection unit 113 outputs a retransmission instruction to the image retransmission request unit 114 to make it retransmit the radiation image (step S105). Note that whether a radiation image corresponding to examination information is stored in the image storage unit 111 may be confirmed as follows. That is, when receiving a radiation image, the control apparatus 105 receives first the data size of the radiation image to be transmitted from the radiation imaging apparatus 104. The control apparatus 105 then receives the transmission start notification of the radiation image, the data of the radiation image, and the transmission termination notification from the radiation imaging apparatus 104. The control apparatus 105 determines whether it has received the radiation image corresponding to the examination information, by comparing the data size of the radiation image received between the transmission start notification of the radiation image to the transmission termination notification with the data size received before the transmission start.

Upon receiving a retransmission instruction, the image retransmission request unit 114 requests the image transmission unit 109 in the radiation imaging apparatus 104 to retransmit the radiation image stored in the image storage unit 108 (step S106). Upon receiving the retransmission request, the image transmission unit 109 reads out the radiation image stored in the image storage unit 108, and starts transmitting the image to the control apparatus 105 again (step S107). The image reception unit 110 receives the radiation image retransmitted from the image transmission unit 109 (step S108). The procedure to be performed after the reception of the retransmitted radiation image by the image reception unit 110 is the same as the normal imaging procedure described above. The retransmission of a radiation image after the detection of an abnormal termination by the abnormal termination detection unit 113 is implemented in the above manner.

As described above, it is determined, based on the storage state of radiation images in the image storage unit 111, whether any unreceived radiation image exists. If an unreceived radiation image exists, the radiation imaging apparatus 104 is requested to retransmit the radiation image. Even if, therefore, an abnormality has occurred during the transfer of a radiation image, it is possible to normally retransmit the radiation image and normally link it to examination information. This can prevent a radiation image loss and suppress ineffective exposure on an object. In addition, it is possible to save the task of re-imaging, and hence to save an operation time of the operator.

Second Embodiment

The first embodiment has exemplified the case in which when determining that an unreceived radiation image exists, the control apparatus 105 immediately requests the radiation imaging apparatus to retransmit the radiation image. The second embodiment will exemplify a case in which when an unreceived radiation image exists, a control apparatus 105 issues a request to retransmit the radiation image after the process of, for example, displaying a corresponding message.

Figure 9:
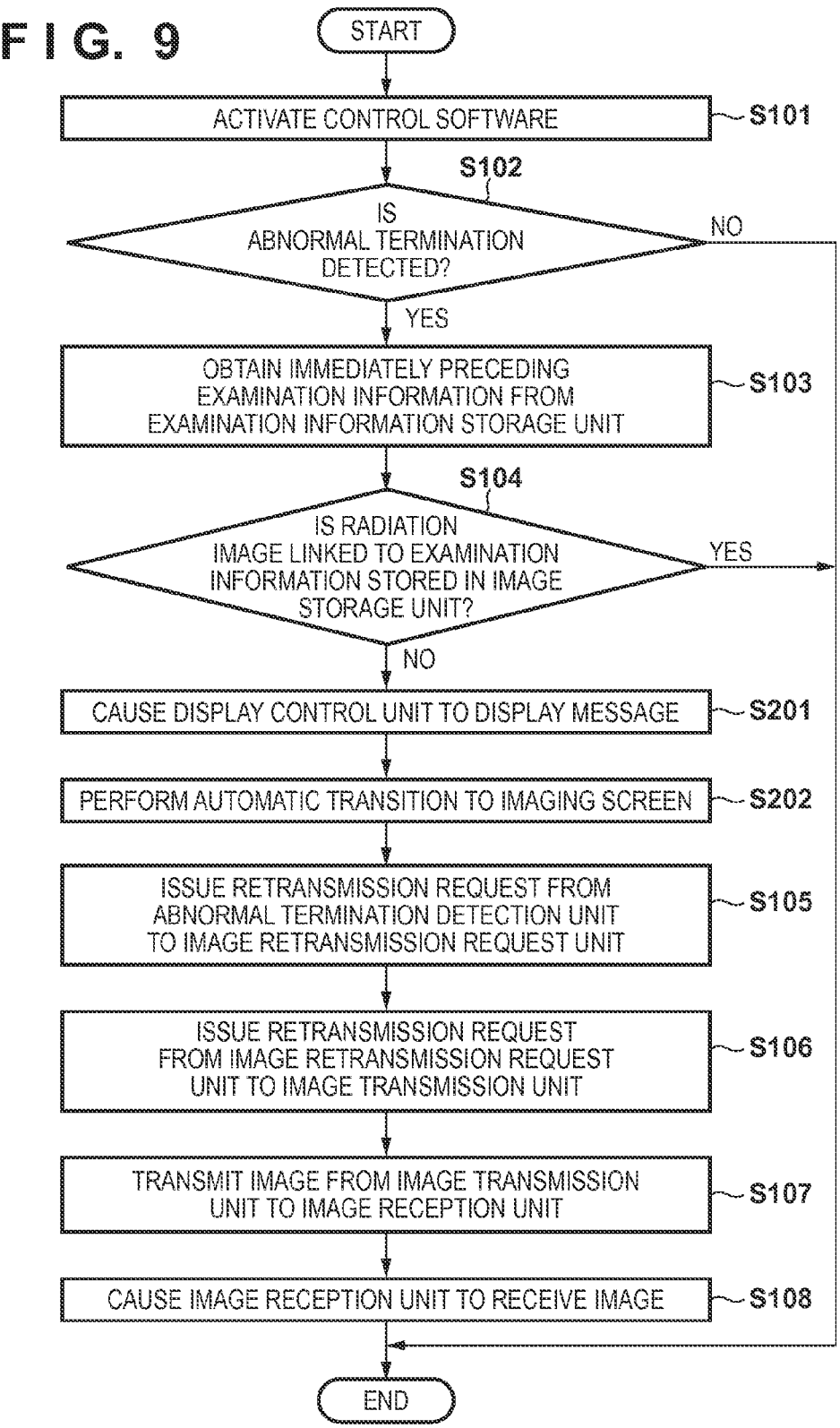
FIG. 9 is a flowchart for explaining the operation of a control apparatus according to the second embodiment.

The arrangement of a radiation imaging system 101 according to the second embodiment is the same as that in the first embodiment (FIG. 1). The operation of the radiation imaging system 101 according to the second embodiment will be described below with reference to the flowchart of FIG. 9. The processing in steps S101 to S108 in FIG. 9 is the same as that in steps S101 to S108 in FIG. 3.

Figure 10:
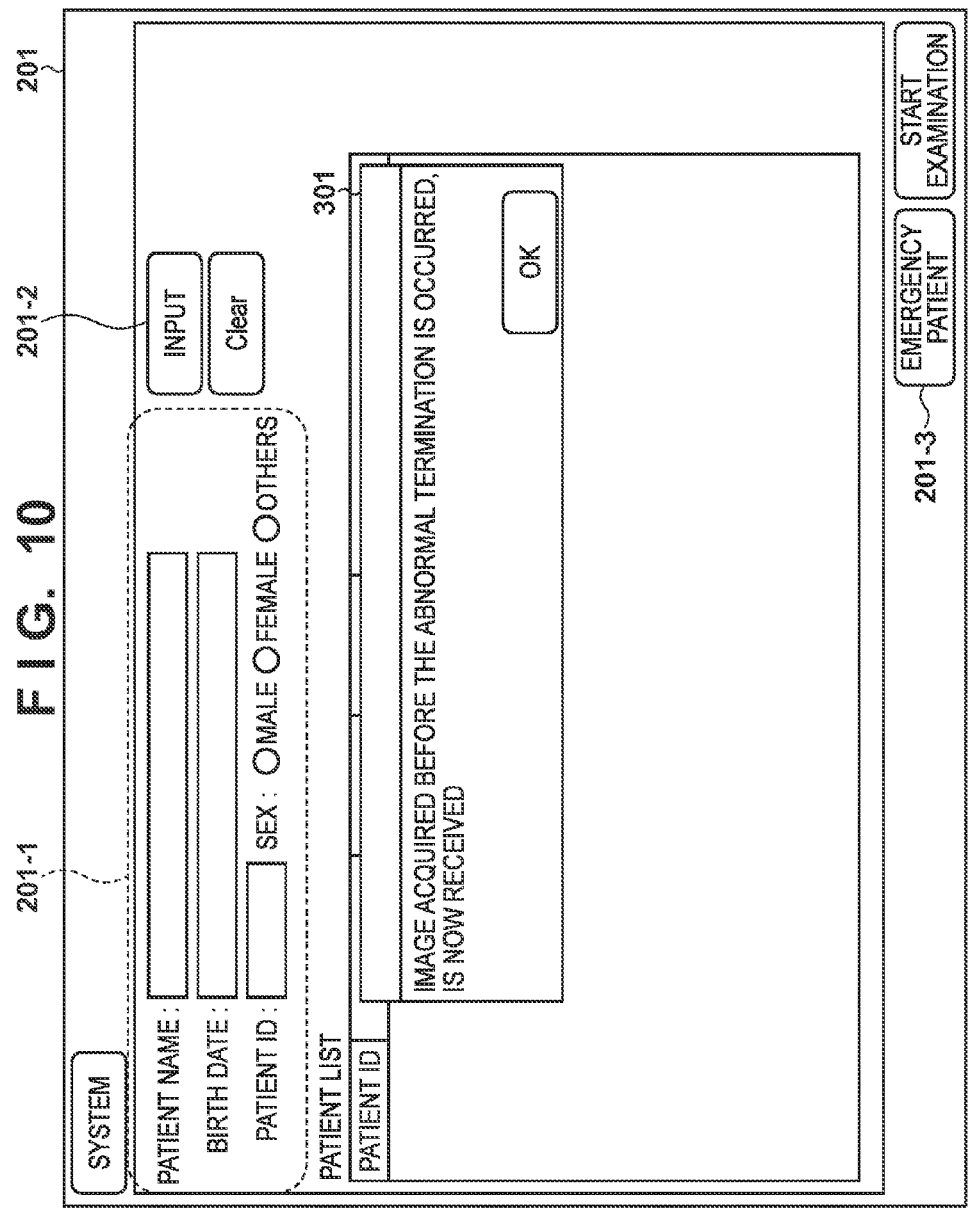
FIG. 10 is a view showing an object information input screen (with a retransmission message)

In step S104, if no radiation image is stored in an image storage unit 111, an abnormal termination detection unit 113 determines that an unreceived radiation image exists. If the abnormal termination detection unit 113 determines that an unreceived radiation image exists, a display control unit 115 displays a message indicating that the immediately previously obtained radiation image is not saved on an object information input screen 201 displayed at the time of the activation of control software 106 (step S201). FIG. 10 shows an example of displaying a message box 301 prompting retransmission on the object information input screen 201. When the operator presses the OK button in the message box 301, the display control unit 115 automatically shifts the scree to an imaging screen 203 (step S202). In this case, as examination information such as object information and an imaging part, the examination information obtained in step S103 is used. That is, the imaging screen 203 is generated and displayed by using examination information input immediately before the abnormal termination detection unit 113 has detected the abnormal termination of the control software 106. In this case, the system may be configured to automatically shift the screen to the imaging screen 203 after the lapse of a predetermined time without arranging the OK button in the message box 301.

The subsequent processing in steps S106 to S108 is the same as that described in the first embodiment. That is, a request to retransmit the radiation image is issued to a radiation imaging apparatus 104, and the retransmitted radiation image is received. Note that in the second embodiment, when the request to retransmit the radiation image is executed on the imaging screen 203 and the retransmission of the radiation image succeeds, the screen shifts to an imaging screen 204. Note, however, that in this case, since only retransmission of the radiation image is executed, the operator does not execute radiation irradiation. The procedure after an image reception unit 110 receives the retransmitted radiation image is the same as the normal imaging procedure described above. The examination information obtained in step S103 and the retransmitted radiation image are managed as relevant data. In this manner, the retransmission of the radiation image after the detection of the abnormal termination by the abnormal termination detection unit 113 is implemented.

According to the second embodiment described above, screen transition and association between examination information and radiation image are performed in the same manner as in the normal imaging procedure. Therefore, the operator can easily confirm by which examination information a radiation image associated at the time of retransmission is generated.

Note that an arrangement which changes the timing of issuing a retransmission request may be configured to start issuing a retransmission request on, for example, the imaging screen 203 in accordance with an operation input from the operator instead of performing this operation at the time of activation. Alternatively, the system may be configured to display a display screen for emergency imaging without issuing a transmission request in response to an input to trigger emergency imaging, thereby saving an untransmitted/unreceived radiation image.

Third Embodiment

The first and second embodiments are based on the assumption that one radiation image is stored in the image storage unit 108 in the radiation imaging apparatus 104. However, this is not exhaustive. An image storage unit 108 of a radiation imaging apparatus 104 may be configured to store a plurality of radiation images. In this case, an image retransmission request unit 114 requests an image transmission unit 109 to retransmit a radiation image, of a plurality of radiation images stored in the image storage unit 108, which corresponds to the newest imaging date and time. Alternatively, the image storage unit 108 may store the examination information transmitted from a control apparatus 105 in association with a radiation image, and the control apparatus 105 may issue a retransmission request upon specifying examination information. This allows the control apparatus 105 to receive a radiation image corresponding to examination information even when the image storage unit 108 can store a plurality of radiation images, thereby reliably implementing retransmission of an obtained image.

Fourth Embodiment

The first to third embodiments are based on the assumption that the number of radiation imaging apparatuses 104 to be simultaneously connected to the control apparatus 105 is one. However, this is not exhaustive. A plurality of radiation imaging apparatuses 104 may be simultaneously connected to the control apparatus 105. In this case, an image retransmission request unit 114 requests an image transmission unit 109 to retransmit a radiation image to the image transmission unit of the radiation imaging apparatus which has been used in the examination executed immediately before the abnormal termination. Such a retransmission request destination is specified based on the identification information of the radiation imaging apparatus which is included in the examination information obtained from an examination information storage unit 112. Note that the identification information of the radiation imaging apparatus is, for example, the identification information of the radiation imaging apparatus selected from an imaging apparatus group 202-1 on an imaging part selecting screen 202 shown in FIG. 5.

Fifth Embodiment

The second embodiment has exemplified the case in which the control apparatus 105 shifts the screen to the imaging screen 203 based on the examination information obtained from the examination information storage unit 112. However, it is not always necessary to use examination information immediately before an abnormal termination. For example, when a control apparatus 105 is activated to image an emergency patient, it is preferable to input the examination information of the emergency patient in preference to examination information at the time of an abnormal termination. According to the fifth embodiment, after a message is displayed in step S201, the screen can be shifted to an object information input screen 201 in accordance with a user operation (selecting whether to immediately perform retransmission or input the examination information of an emergency patient).

The operation to be performed when immediately performing retransmission is the same as that in the second embodiment. When selecting to input the examination information of an emergency patient, the object information input screen 201 is displayed. The operator then inputs the information of the emergency patient on the object information input screen 201, and selects an imaging part on an imaging part selecting screen 202. After the screen shifts to an imaging screen 203, an image retransmission request unit 114 requests an image transmission unit 109 to retransmit a radiation image. In this case, the retransmitted radiation image is stored as data relevant to arbitrary examination information used at the time of emergency patient imaging. However, control software 106 according this embodiment has a function of replacing the radiation image stored in an image storage unit 111 with different examination information stored in an examination information storage unit 112.

Figure 15:
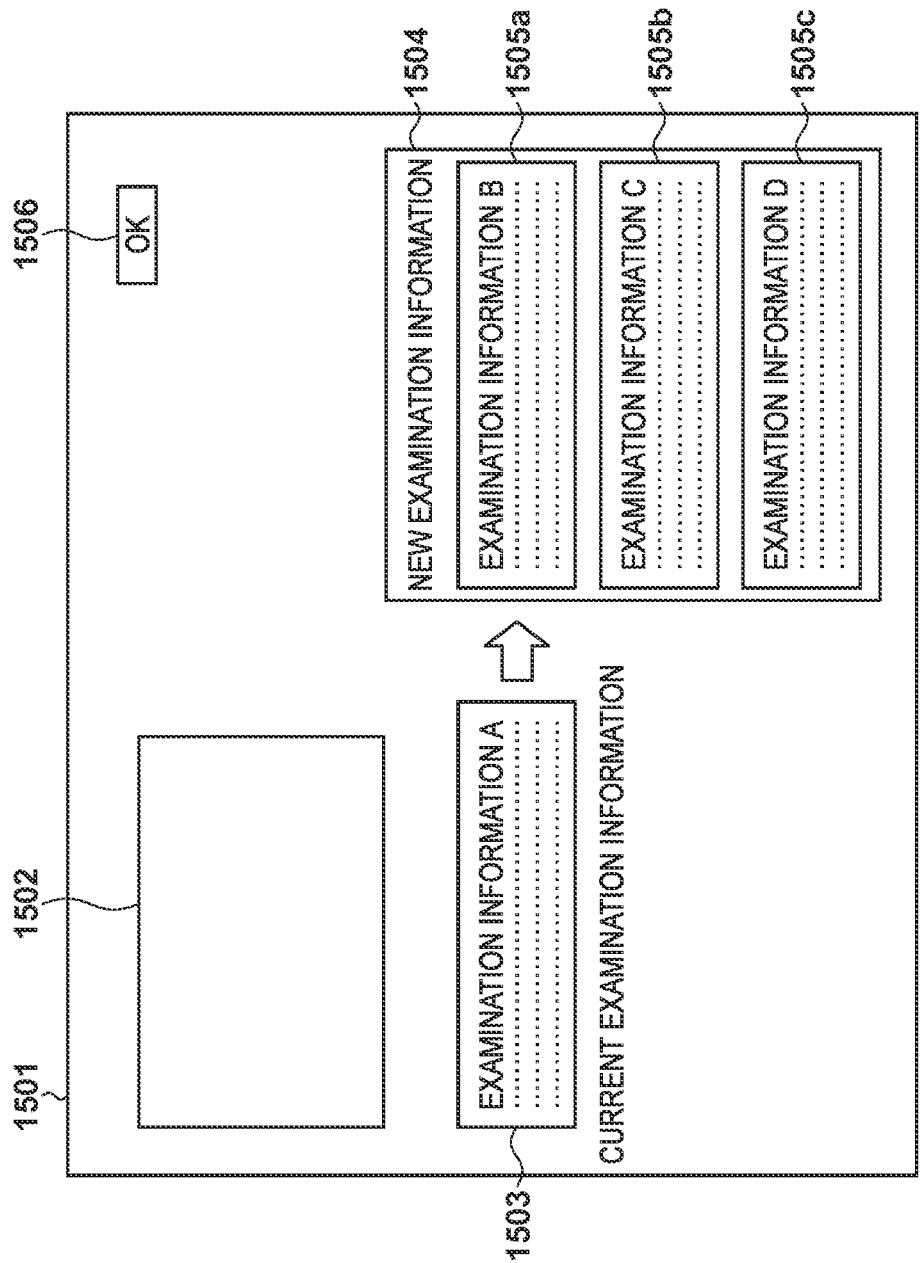
FIG. 15 is a view for explaining an example of a replacement screen according to the fifth embodiment.

For example, according to this embodiment, it is possible to replace examination information with correct examination information afterward via a replacement screen (display window 1501) like that shown in FIG. 15 which is displayed on a display apparatus 107 by a display control unit 115. The display window 1501 displays a thumbnail image of the radiation image stored in the image storage unit 111 in an image area 1502, displays current examination information in an area 1503, and displays examination information candidates 1505 in an area 1504. In the case shown in FIG. 15, examination information A is displayed as current examination information in the area 1503, and pieces of examination information 1505a, 1505b, and 1505c (examination information B, C, and D) are displayed as examination information candidates to replace in the area 1504 in the order named. In addition, on this replacement screen, the examination information (examination information B displayed in the examination information block 1505a in FIG. 15) used immediately before the detection of an abnormal termination by an abnormal termination detection unit 113 is preferentially displayed. Therefore, the examination information of an emergency patient is displayed as examination information A in the area 1503 before replacement of patient information, and the examination information used immediately before the detection of the abnormal termination is displayed as examination information B in the area 1504. Upon selecting examination information B and then pressing an OK button 1506, the user can replace the examination information of the radiation image corresponding to the thumbnail image displayed in the image area 1502, which is examination information A (the examination information of the emergency patient), with examination information B (the examination information immediately before the detection of the abnormal termination).

Sixth Embodiment

The first to fifth embodiments have exemplified the arrangement configured to make the control apparatus 105 determine whether any unreceived radiation image exists, and to transmit the radiation image stored in the radiation imaging apparatus 104 in accordance with a retransmission instruction from the control apparatus 105. The sixth embodiment will exemplify an arrangement configured to make a radiation imaging apparatus 104 determine the existence of a radiation image which has not been transmitted to a control apparatus 105 and initiate retransmission.

Figure 11:
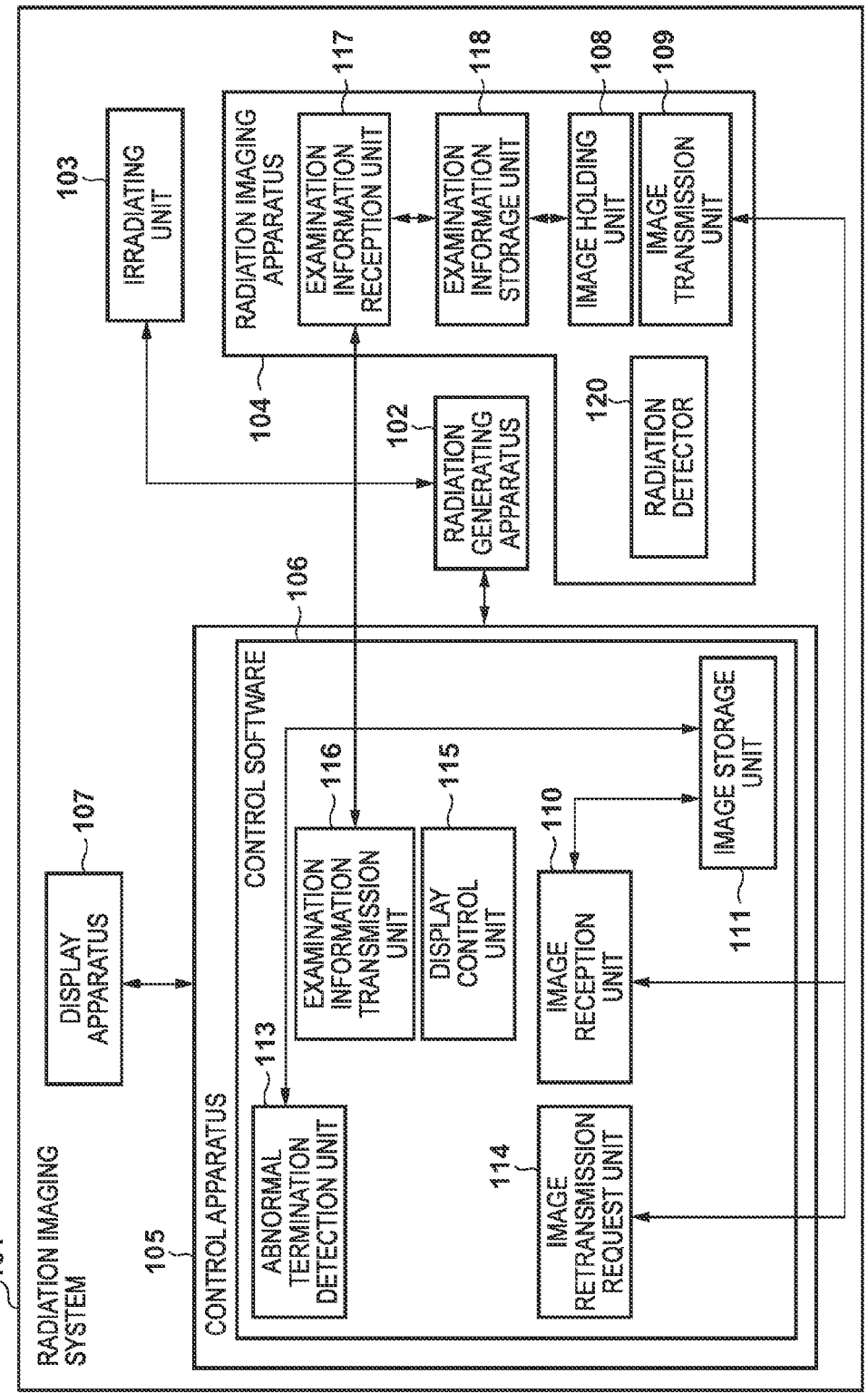
FIG. 11 is a block diagram showing an example of the arrangement of a radiation imaging system according to the sixth embodiment.

FIG. 11 is a block diagram showing an example of the system configuration of a radiation imaging system 101 according to the sixth embodiment. As shown in FIG. 11, the radiation imaging system 101 according to the sixth embodiment includes an examination information transmission unit 116 added to the control apparatus 105. The examination information transmission unit 116 transmits the examination information input via a display apparatus 107 to the radiation imaging apparatus 104. In the radiation imaging apparatus 104, an examination information reception unit 117 receives the examination information transmitted from the examination information transmission unit 116. An examination information storage unit 118 stores the examination information received by the examination information reception unit 117.

Figure 12:
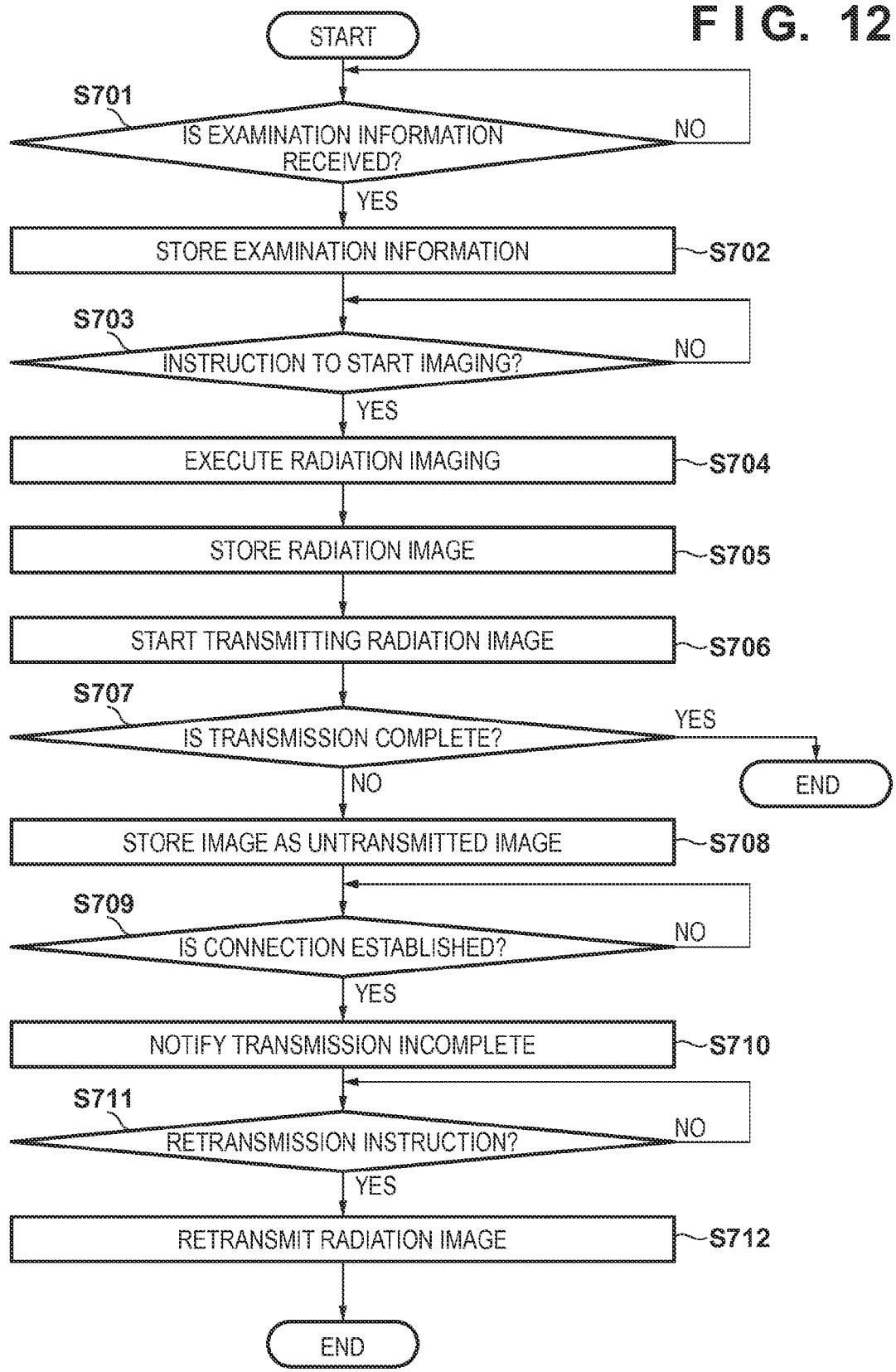
FIG. 12 is a flowchart for explaining the operation of a radiation imaging apparatus according to the sixth embodiment.

FIG. 12 is a flowchart for explaining the operation of the radiation imaging apparatus 104 according to the sixth embodiment. The radiation imaging system 101 according to the sixth embodiment stores examination information in the radiation imaging apparatus 104 instead of the control apparatus 105. That is, the examination information transmission unit 116 transmits the examination information input via the display apparatus 107 to the examination information reception unit 117, and stores the examination information received by the examination information reception unit 117 in the examination information storage unit 118 (steps S701 and S702). The radiation imaging apparatus 104 obtains a radiation image in accordance with an imaging instruction from the control apparatus 105 (step S704), and stores the obtained radiation image in the image storage unit 108 in association with the examination information stored in the examination information storage unit 118 (step S705).

With this operation, it is possible to manage a radiation image and examination information as relevant data in the radiation imaging apparatus 104 instead of the control apparatus 105. It is therefore unnecessary for an abnormal termination detection unit 113 to obtain the examination information used in step S103. In addition, when the above radiation image is retransmitted, since the examination information is stored in the radiation imaging apparatus 104 as data relevant to the radiation image, it is possible to simultaneously receive the radiation image and the examination information.

An image transmission unit 109 of the radiation imaging apparatus 104 transmits the radiation image stored in an image storage unit 108 to the control apparatus 105 (step S706). When the completion of the transmission of the radiation image is confirmed, this processing is terminated (step S707). Note that the confirmation of transmission completion can be performed depending on whether a reception completion notice can be received from the control apparatus 105 within a predetermined time since the transmission of the last packet. If no transmission completion notice can be confirmed, the corresponding radiation image is stored as an untransmitted image (step S708). Note that determination of transmission completion/transmission incompletion may be performed based on, for example, whether the confirmation of the transmission completion of a radiation image is obtained from the control apparatus 105 within a predetermined time.

Subsequently, upon detecting re-connection to the control apparatus 105 (step S709), the radiation imaging apparatus 104 notifies the control apparatus 105 that an untransmitted radiation image exists (step S710), and waits for a retransmission instruction from the control apparatus 105 (step S711). When a retransmission instruction is issued, the radiation imaging apparatus 104 transmits (retransmits) the radiation image stored as an image which has not been transmitted to the control apparatus 105 (step S712).

As described above, according to the sixth embodiment, it is possible to determine the necessity of retransmission on the radiation imaging apparatus 104 side, and the processing load on the control apparatus 105 is reduced.

Seventh Embodiment

The above embodiments are based on the assumption that a radiation image is retransmitted to the same control apparatus. The seventh embodiment will exemplify an arrangement in which after a control apparatus 105 is abnormally terminated, a radiation image is transmitted to another control apparatus. This arrangement will be described with reference to FIG. 11.

Figure 13:
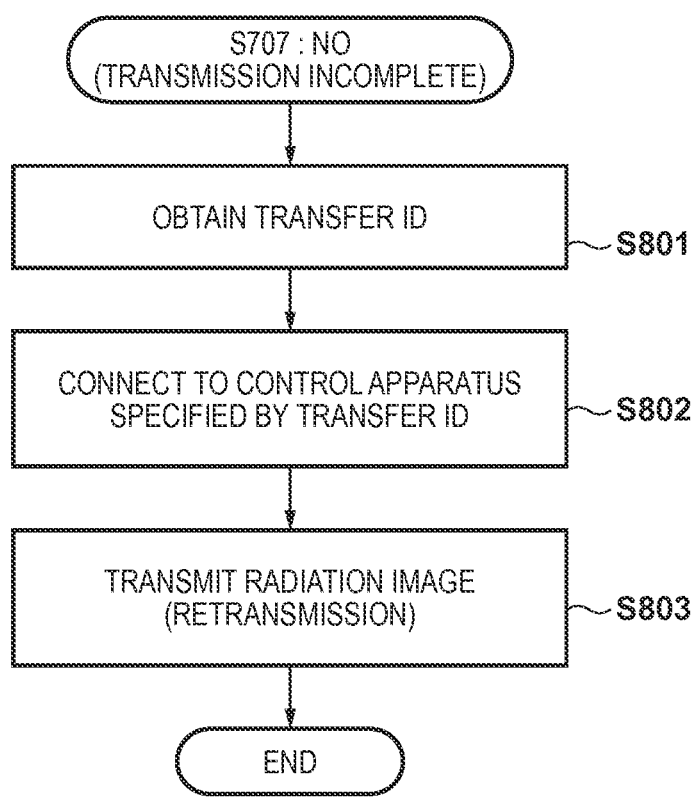
FIG. 13 is a flowchart for explaining the operation of a radiation imaging apparatus according to the seventh embodiment.

An examination information transmission unit 116 transmits the identification information (transfer ID) of a control apparatus at the transfer destination to a radiation imaging apparatus 104, in addition to examination information. Upon receiving this transfer ID, an examination information reception unit 117 stores it in an examination information storage unit 118. FIG. 13 is a flowchart for explaining processing according to the seventh embodiment when NO is obtained in step S707 in FIG. 12, that is, when an untransmitted radiation image exists. The processing in steps S801 to S803 in FIG. 13 is executed instead of the processing in steps S708 to S712 in FIG. 12.

If the transmission of a radiation image to the control apparatus 105 has failed, the radiation imaging apparatus 104 reads out the transfer ID stored in the examination information storage unit 118 (step S801), and establishes a communication connection to another control apparatus specified by the transfer ID (step S802). The radiation imaging apparatus 104 then reads out the examination information stored in the examination information storage unit 118 and the untransmitted radiation image stored in an image storage unit 108, and transmits them to another control apparatus (step S803).

According to the seventh embodiment, when the control apparatus 105 is abnormally terminated during the transmission of a radiation image, there is no need to wait for the restoration of the apparatus. Assume that it is determined in step S707 that the radiation image has not been transmitted. In this case, if a transfer ID is included in the examination information, the processing in FIG. 13 (steps S801 to S803) is executed. If no transfer ID is included in the examination information, the processing in steps S708 to S712 in FIG. 12 may be executed.

Eighth Embodiment

According to the eighth embodiment, a radiation imaging apparatus 104 establishes a connection to another control apparatus. However, this is not exhaustive. For example, even if the transmission of a radiation image to a control apparatus 105 has failed, and it takes much time to reactivate the control apparatus 105, the operator may activate another control apparatus to recover the untransmitted radiation image.

Figure 14:
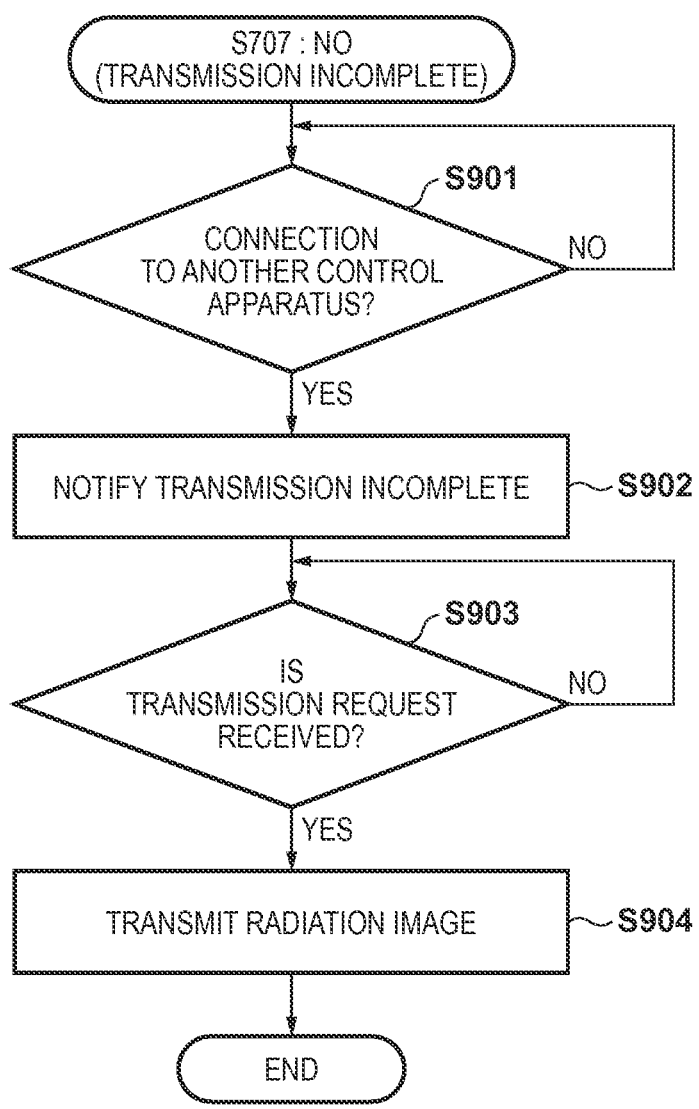
FIG. 14 is a flowchart for explaining the operation of a radiation imaging apparatus according to the eighth embodiment.

According to the eighth embodiment, in a radiation imaging system 101 shown in FIG. 11, an examination information transmission unit 116 transmits the identification information of an imaging order (imaging order ID) to the radiation imaging apparatus 104, in addition to examination information. Upon receiving this imaging order ID, an examination information reception unit 117 stores it in an examination information storage unit 118. FIG. 14 is a flowchart for explaining processing according to the eighth embodiment when NO is obtained in step S707 in FIG. 12, that is, when an untransmitted radiation image exists.

If a radiation image has not been transmitted, the radiation imaging apparatus 104 waits for a new connection to an external apparatus other than the control apparatus 105 (step S901). It is possible to determine whether the external apparatus is other than the control apparatus 105, by using the identification information or the like of the connected external apparatus. When a new connection is established to the external apparatus, the radiation imaging apparatus 104 notifies the control apparatus that an untransmitted radiation image exists (step S902), and waits for a transmission request from the external apparatus (step S903). Upon receiving a transmission request, the radiation imaging apparatus 104 transmits the imaging order ID stored in the examination information storage unit 118 and the untransmitted radiation image stored in the image storage unit 108 to the external apparatus to which a new connection has been established in step S901 (step S904).

Upon receiving the imaging order ID and the radiation image, the external apparatus can obtain an imaging order from, for example, an RIS (Radiology Information System) based on the transmitted imaging order ID, and execute termination processing for the imaging order or transfer the radiation image and the imaging order to a PACS (Picture Archiving and Communication System).

As has been described above, the radiation imaging system according to each embodiment can normally retransmit a radiation image even at the occurrence of an abnormality during the transmission of a radiation image, and normally link the image to examination information. This makes it possible to prevent a radiation image loss and to suppress ineffective exposure on an object. In addition, it is possible to save the task of re-imaging, and hence to save an operation time of the operator.

Note that in each embodiment described above, the control apparatus 105 and the radiation imaging apparatus 104 may be connected via the NIC 156 and a network such as the Internet. In this case, the control apparatus 105 and the radiation imaging apparatus 104 may exist in remote places such as different countries.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-073730, filed Mar. 31, 2014, which is hereby incorporated by reference herein in its entirety.

What is claimed is:

1. A control apparatus which receives a radiation image from a radiation imaging apparatus, the control apparatus comprising:
   a storage unit configured to store examination information and a radiation image received from the radiation imaging apparatus in accordance with the examination information;
   a determination unit configured to determine whether any unreceived radiation image exists, at the time of activation, based on a storage state of a radiation image corresponding to the examination information in the storage unit; and
   a request unit configured to request, in response to a predetermined operation input from a user, the radiation imaging apparatus to transmit a radiation image when the determination unit determines that the unreceived radiation image exists.

2. The apparatus according to claim 1, wherein the determination unit further determines, at the time of activation, whether a previous termination is an abnormal termination, and determines whether the unreceived radiation image exists, upon determining that the previous termination is an abnormal termination.

3. The apparatus according to claim 1, wherein the determination unit determines whether the unreceived radiation image exists, if a radiation image corresponding to the examination information is not stored in the storage unit.

4. The apparatus according to claim 3, wherein the request unit requests the radiation imaging apparatus to transmit a radiation image corresponding to the examination information.

5. The apparatus according to claim 1, further comprising a display unit configured to display a message if the determination unit determines that an unreceived radiation image exists.

6. The apparatus according to claim 1, wherein the request unit transmits a radiation image corresponding to a newest imaging date and time to the radiation imaging apparatus.

7. The apparatus according to claim 1, wherein the request unit requests an imaging apparatus, of a plurality of imaging apparatuses connected to the control apparatus, which is specified by identification information included in the examination information to retransmit a radiation image.

8. The apparatus according to claim 1, wherein the request unit requests a radiation imaging apparatus used in an examination executed at the time of a previous termination to transmit a radiation image.

9. The apparatus according to claim 1, wherein the predetermined operation includes an input of examination information concerning another patient and an examination start instruction.

10. A radiation imaging apparatus comprising:
    a storage unit configured to store a radiation image obtained by radiation imaging;
    a determination unit configured to determine whether an untransmitted radiation image exists in the storage unit, establishing a communication connection to a control apparatus; and
    a transmitting unit configured to transmit the untransmitted radiation image to the control apparatus in response to a predetermined operation by a user, if the determination unit determines that an untransmitted radiation image exists.

11. The apparatus according to claim 10, wherein the storage unit stores examination information obtained from the control apparatus and the radiation image obtained by radiation imaging in association with each other, and
    the transmitting unit transmits the untransmitted radiation image and the examination information associated with the radiation image to the control apparatus.

12. A radiation imaging apparatus which transmits an obtained radiation image to a control apparatus, the apparatus comprising:
- a receiving unit configured to receive identification information of an apparatus at a transfer destination from the control apparatus;
- a storage unit configured to store a radiation image obtained by radiation imaging; and
- a transmitting unit configured to transmit the stored radiation image to the apparatus at the transfer destination based on the identification information, when transmission of the radiation image stored in the storage unit to the control apparatus fails.

13. A radiation imaging apparatus which transmits an obtained radiation image to a control apparatus, the apparatus comprising:
- a receiving unit configured to receive identification information of an imaging order from the control apparatus;
- a storage unit configured to store a radiation image obtained by radiation imaging and the identification information in association with each other; and
- a transmitting unit configured to transmit the stored radiation image and the identification information to an external apparatus in accordance with a transmission request of the radiation image from the external apparatus, when transmission of the radiation image stored in the storage unit to the control apparatus fails.

14. A control method for a control apparatus which receives a radiation image from a radiation imaging apparatus, the method comprising:
- determining whether an unreceived radiation image to be received from the radiation imaging apparatus exists, at the time of activation; and
- requesting, in response to a predetermined operation input from a user, the radiation imaging apparatus to transmit a radiation image, if it is determined that the unreceived radiation image exists.

15. A control method for a radiation imaging apparatus which transmits an obtained radiation image to a control apparatus, the method comprising:
- receiving identification information of an apparatus at a transfer destination from the control apparatus;
- storing a radiation image obtained by radiation imaging in a storage unit; and
- transmitting the stored radiation image to the apparatus at the transfer destination based on the identification information, when transmission of the radiation image stored in the storage unit to the control apparatus fails.

16. A control method for a radiation imaging apparatus which transmits an obtained radiation image to a control apparatus, the method comprising:
- receiving identification information of an imaging order from the control apparatus;
- storing a radiation image obtained by radiation imaging and the identification information in a storage unit in association with each other; and
- transmitting the stored radiation image and the identification information to an external apparatus in accordance with a transmission request of the radiation image from the external apparatus, when transmission of the radiation image stored in the storage unit to the control apparatus fails.

17. A radiation imaging system in which a control apparatus receives a radiation image from a radiation imaging apparatus via a network,
the control apparatus comprising:
- a determination unit configured to determine, at the time of activation, whether an unreceived radiation image to be received from the radiation imaging apparatus exists; and
- a request unit configured to request, in response to a predetermined operation input from a user, the radiation imaging apparatus to transmit a radiation image when the determination unit determines that the unreceived radiation image exists.

18. A radiation imaging system in which a control apparatus receives a radiation image from a radiation imaging apparatus via a network,
the radiation imaging apparatus comprising:
- a receiving unit configured to receive identification information of an apparatus at a transfer destination from the control apparatus;
- a storage unit configured to store a radiation image obtained by radiation imaging; and
- a transmitting unit configured to transmit the stored radiation image to the apparatus at the transfer destination based on the identification information, when transmission of the radiation image stored in the storage unit to the control apparatus fails.

19. A radiation imaging system in which a control apparatus receives a radiation image from a radiation imaging apparatus via a network, the radiation imaging apparatus comprising:
- a receiving unit configured to receive identification information of an imaging order from the control apparatus;
- a storage unit configured to store a radiation image obtained by radiation imaging and the identification information in association with each other; and
- a transmitting unit configured to transmit the stored radiation image and the identification information to an external apparatus in accordance with a transmission request of the radiation image from the external apparatus, when transmission of the radiation image stored in the storage unit to the control apparatus fails.

20. A non-transitory computer readable storage medium storing a program for causing a computer to execute each step in a control method for a control apparatus which receives a radiation image from a radiation imaging apparatus, the method comprising:
- determining whether an unreceived radiation image to be received from the radiation imaging apparatus exists, at the time of activation; and
- requesting, in response to a predetermined operation input from a user, the radiation imaging apparatus to transmit a radiation image, if it is determined that the unreceived radiation image exists.

21. A non-transitory computer readable storage medium storing a program for causing a computer to execute each step in a control method for a radiation imaging apparatus which transmits an obtained radiation image to a control apparatus, the method comprising:
- receiving identification information of an apparatus at a transfer destination from the control apparatus;
- storing a radiation image obtained by radiation imaging in a storage unit; and
- transmitting the stored radiation image to the apparatus at the transfer destination based on the identification information, when transmission of the radiation image stored in the storage unit to the control apparatus fails.

22. A non-transitory computer readable storage medium storing a program for causing a computer to execute each step in a control method for a radiation imaging apparatus which transmits an obtained radiation image to a control apparatus, the method comprising:
- receiving identification information of an imaging order from the control apparatus;
- storing a radiation image obtained by radiation imaging and the identification information in a storage unit in association with each other; and
- transmitting the stored radiation image and the identification information to an external apparatus in accordance with a transmission request of the radiation image from the external apparatus, when transmission of the radiation image stored in the storage unit to the control apparatus fails.

* * * * *